June 10, 1952 J. A. ARMSTRONG Plant Pat. 1,104
ROSE PLANT
Filed Dec. 29, 1950
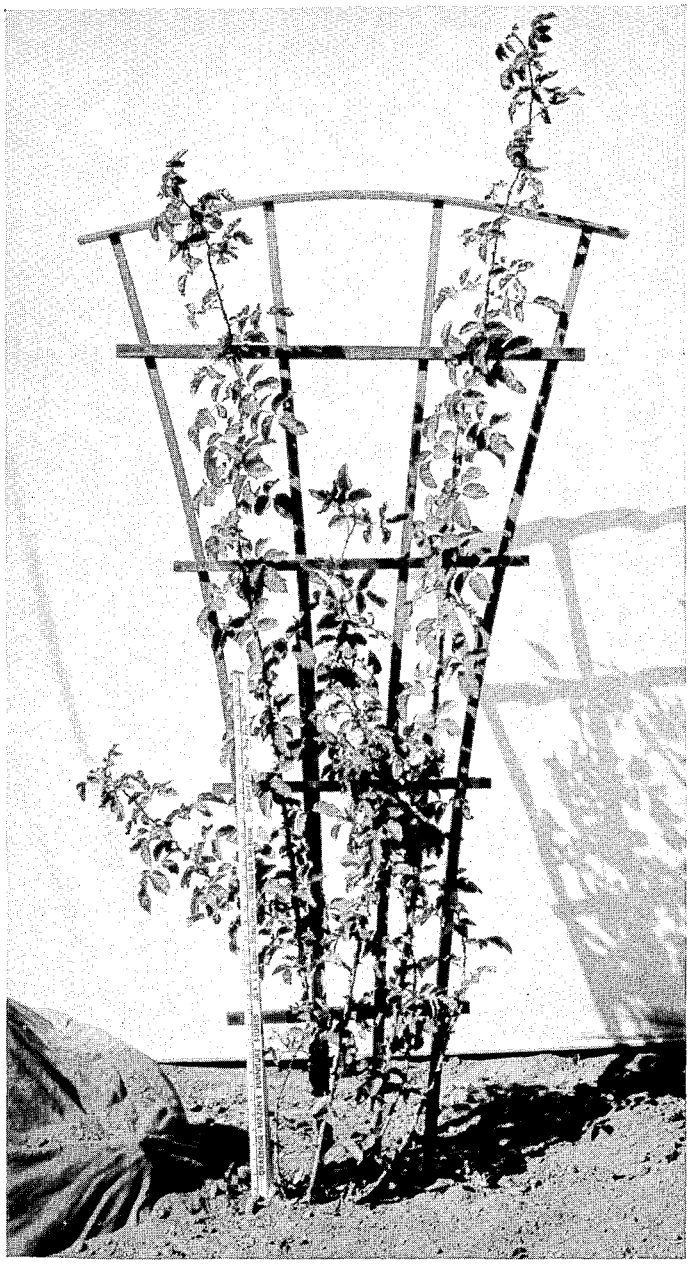
Inventor.
J. A. Armstrong
By: Robbins Cook
attorneys.

Patented June 10, 1952

Plant Pat. 1,104

UNITED STATES PATENT OFFICE 1,104

ROSE PLANT

John A. Armstrong, Ontario, Calif., assignor to Armstrong Nurseries, Inc., Ontario, Calif., a corporation of California Application December 29, 1950, Serial No. 203,445

1 Claim. (Cl. 47—61)

The present invention relates to a new and distinct variety of rose plant of the climbing hybrid tea class, originating as a bud sport of the variety "Taffeta" (Plant Patent No. 716), and dominantly distinguished therefrom by its climbing habit of growth. The new variety was discovered by me in a cultivated nursery row of "Taffeta" plants growing in the fields of the assignee hereof, at Ontario, California.

The parent variety is a bush rose of the hybrid tea class, and is primarily notable for its habit and vigor of growth corresponding to its pollen parent, for its glossy foliage that is resistant to mildew, the red color of its new growth, the heavy and large size of both its new and mature foilage, its freedom of bloom, and for its attractive shape and form of bud, as well as the unusual color of its flowers. However, this bush variety, so far as I am aware, has never exhibited a climbing habit, and its growth has been that of the average strong bush rose, and usually attains a height of only 3½ to 4½ feet.

The new variety is substantially identical with its parent, except that it is definitely a climber, as evidenced by its strong canes which attain a height at maturity of 10 to 14 feet or more, and in addition, it is characterized by its habit of producing many more flowers in the spring than can usually be found at any one time on the bush variety "Taffeta," with an intermittent flowering habit during the remainder of the growing season.

Other differences of relatively lesser importance may be noted in respect to the new variety, such as:

(1) Its flowers usually average slightly larger in size than those of the parent, that is, from 3¼ to 4 inches;

(2) Its petals usually range slightly greater in number, such as from 16 to 25 petals, plus 3 to 7 petaloids, arranged regularly, and with the tips of the petals rolled loosely outward at maturity;

(3) The rachis of its foliage is grooved on its upper side; and (4) Its habit of growth is characterized by its little branched, heavy, vigorous canes.

In view of the similarities in general characteristics between the new variety and its parent, it is unnecessary to describe the new variety in detail since, except for the aforementioned distinctions, it substantially conforms to the detailed description contained in the above-noted patent, to which reference may be readily had.

Asexual reproduction of the new variety by budding at Ontario, California, shows that the foregoing characteristics come true to form and are established and transmitted through succeeding propagations.

The accompanying drawing shows a specimen plant of the new variety in association with a marked scale having the form of a yard-stick, and illustrates the typical climbing habit of growth of the new variety.

I claim:

A new and distinct variety of rose plant of the climbing hybrid tea class, characterized by being substantially identical with its parent "Taffeta" (Plant Patent No. 716), but essentially distinguished therefrom by its climbing habit of growth, by its habit of producing many more flowers in the spring than can usually be found at any one time on the bush parent, and by its intermittent flowering habit during the remainder of the growing season, substantially as shown and described herein.

JOHN A. ARMSTRONG.

No references cited.